United States Patent
Yoshino

(10) Patent No.: US 9,661,998 B2
(45) Date of Patent: May 30, 2017

(54) SCANNING ENDOSCOPE WITH VIBRATION ABSORBING MEMBER

(71) Applicant: OLYMPUS CORPORATION, Tokyo (JP)

(72) Inventor: Masahiro Yoshino, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/850,384

(22) Filed: Sep. 10, 2015

(65) Prior Publication Data

US 2015/0374219 A1    Dec. 31, 2015

Related U.S. Application Data

(63) Continuation of application No. PCT/JP2014/059453, filed on Mar. 31, 2014.

(30) Foreign Application Priority Data

Jul. 12, 2013    (JP) .................. 2013-146851

(51) Int. Cl.
*A61B 1/07* (2006.01)
*A61B 1/00* (2006.01)
(Continued)

(52) U.S. Cl.
CPC ............ *A61B 1/07* (2013.01); *A61B 1/00096* (2013.01); *A61B 1/00126* (2013.01);
(Continued)

(58) Field of Classification Search
CPC ..... A61B 1/07; A61B 1/00172; A61B 1/0669; A61B 1/0623; A61B 5/0062;
(Continued)

(56) References Cited

U.S. PATENT DOCUMENTS 6,023,406 A * 2/2000 Kinoshita ................ H01G 5/12
                                                                 333/139
7,129,472 B1 * 10/2006 Okawa ............... A61B 1/00059
                                                                  250/216
(Continued)

FOREIGN PATENT DOCUMENTS

EP         1929939 A2    6/2008
JP    2001-174744 A      6/2001
(Continued)

OTHER PUBLICATIONS

International Search Report dated Jun. 10, 2014 issued in PCT/JP2014/059453.
(Continued)

*Primary Examiner* — John P Leubecker
(74) *Attorney, Agent, or Firm* — Scully, Scott, Murphy & Presser, P.C.

(57) ABSTRACT

A scanning endoscope includes: an optical fiber that guides illumination light for illuminating an object from a proximal end thereof and emits the illumination light from a distal end thereof; an actuator portion provided on a side portion of the optical fiber, for causing the distal end of the optical fiber to oscillate; a holding portion provided on a more proximal end side of the optical fiber than the actuator portion, for holding the optical fiber so as to allow the distal end of the optical fiber to oscillate with the actuator portion; a vibration-absorbing member formed so as to cover a circumference of a part of the optical fiber, the part being located on a more proximal end side than the holding portion and adjacent to the holding portion; and an outer cover that covers a circumference of at least a part of the vibration-absorbing member.

3 Claims, 4 Drawing Sheets

(51) Int. Cl.
  *A61B 1/06* (2006.01)
  *H01L 41/09* (2006.01)
  *A61B 5/00* (2006.01)
(52) U.S. Cl.
  CPC ...... *A61B 1/00133* (2013.01); *A61B 1/00172* (2013.01); *A61B 1/0669* (2013.01); *A61B 5/0062* (2013.01); *H01L 41/0913* (2013.01)
(58) Field of Classification Search
  CPC ... A61B 5/0066; A61B 5/0068; H01L 41/053; H01L 41/0533; H01L 41/0536; H01L 41/0906; H01L 41/0913
  See application file for complete search history.

(56) References Cited

U.S. PATENT DOCUMENTS

| | | | | |
|---|---|---|---|---|
| 2005/0052753 | A1* | 3/2005 | Kanai | A61B 1/0008 359/642 |
| 2008/0081950 | A1 | 4/2008 | Koenig et al. | |
| 2009/0316116 | A1* | 12/2009 | Melville | A61B 1/0008 353/31 |
| 2010/0179386 | A1* | 7/2010 | Kobayashi | A61B 1/0008 600/178 |
| 2011/0054252 | A1* | 3/2011 | Ozaki | A61B 1/00089 600/109 |
| 2013/0257222 | A1* | 10/2013 | Funakubo | H01L 41/047 310/317 |
| 2013/0345508 | A1* | 12/2013 | Akui | A61B 1/00172 600/109 |
| 2014/0177021 | A1* | 6/2014 | Shimamoto | G02B 21/0044 359/200.7 |
| 2014/0300901 | A1* | 10/2014 | Cha | G01B 9/0205 356/479 |
| 2016/0004072 | A1* | 1/2016 | Kasai | A61B 1/00172 250/227.26 |
| 2016/0216510 | A1* | 7/2016 | Tsuruta | G01N 21/474 |

FOREIGN PATENT DOCUMENTS

| | | |
|---|---|---|
| JP | 2008-100057 A | 5/2008 |
| JP | 2009-212519 A | 9/2009 |
| JP | 2011-139781 A | 7/2011 |
| JP | 2012-148062 A | 8/2012 |
| JP | 2013-121455 A | 6/2013 |
| WO | WO 2012/090642 A1 | 7/2012 |

OTHER PUBLICATIONS

Japanese Office Action dated Mar. 3, 2015 issued in JP 2014-557929.

* cited by examiner

SCANNING ENDOSCOPE WITH VIBRATION ABSORBING MEMBER

CROSS REFERENCE TO RELATED APPLICATION

This application is a continuation application of PCT/JP2014/059453 filed on Mar. 31, 2014 and claims benefit of Japanese Application No. 2013-146851 filed in Japan on Jul. 12, 2013, the entire contents of which are incorporated herein by this reference.

BACKGROUND OF THE INVENTION

1. Field of the Invention

The present invention relates to a scanning endoscope, and more particularly to a scanning endoscope that acquires an image by scanning an object.

2. Description of the Related Art

Various kinds of techniques for reducing a diameter size of an insertion portion to be inserted into a body cavity of a subject to be examined are proposed for endoscopes in medical fields, in order to alleviate a burden on the subject to be examined. As an apparatus which belongs to such techniques, there has been conventionally known a scanning endoscope which does not include a solid-state image pickup device at a portion corresponding to the insertion portion as described above, for example.

Specifically, the above-described scanning endoscope is configured, for example; to cause an actuator, which is mounted to the light-emission-side end portion of an illumination fiber that transmits illumination light emitted from a light source portion, to vibrate. This vibration causes the illumination fiber to oscillate in a predetermined scanning pattern, thereby enabling scanning of an object in a scanning range corresponding to the predetermined scanning pattern. Japanese Patent Application Laid-Open Publication No. 2009-212519 discloses a scanning fiber endoscope having a configuration similar to that of the above-described scanning endoscope.

SUMMARY OF THE INVENTION

A scanning endoscope according to one aspect of the present invention includes: an optical fiber that guides illumination light for illuminating an object from a proximal end thereof and emits the illumination light from a distal end thereof; an actuator portion that causes the distal end of the optical fiber to oscillate, the actuator portion being provided on a side portion of the optical fiber; a holding portion that holds the optical fiber so as to allow the distal end of the optical fiber to oscillate with the actuator portion, the holding portion being provided on a more proximal end side of the optical fiber than the actuator portion; a vibration-absorbing member formed so as to cover a circumference of a part of the optical fiber, the part being located on a more proximal end side than the holding portion and adjacent to the holding portion, the vibration-absorbing member being made of a material that absorbs vibration; and an outer cover that covers a circumference of at least a part of the vibration-absorbing member.

A scanning endoscope according to another one aspect of the present invention includes: an optical fiber that guides illumination light for illuminating an object from a proximal end thereof and emits the illumination light from a distal end thereof; an actuator portion that causes the distal end of the optical fiber to oscillate, the actuator portion being provided on a side portion of the optical fiber; a holding portion that holds the optical fiber so as to allow the distal end of the optical fiber to oscillate with the actuator portion, the holding portion being provided on a more proximal end side of the optical fiber than the actuator portion, wherein an outer diameter of a first part of the optical fiber and an outer diameter of a second part of the optical fiber are different from each other, the first part of the optical fiber being adjacent to the holding portion and located on a more proximal end side than the holding portion and the second part of the optical fiber being located on a more distal end side than the first part.

DETAILED DESCRIPTION OF THE PREFERRED EMBODIMENTS

Hereinafter, embodiments of the present invention will be described with reference to drawings.

First Embodiment

Figure 1:
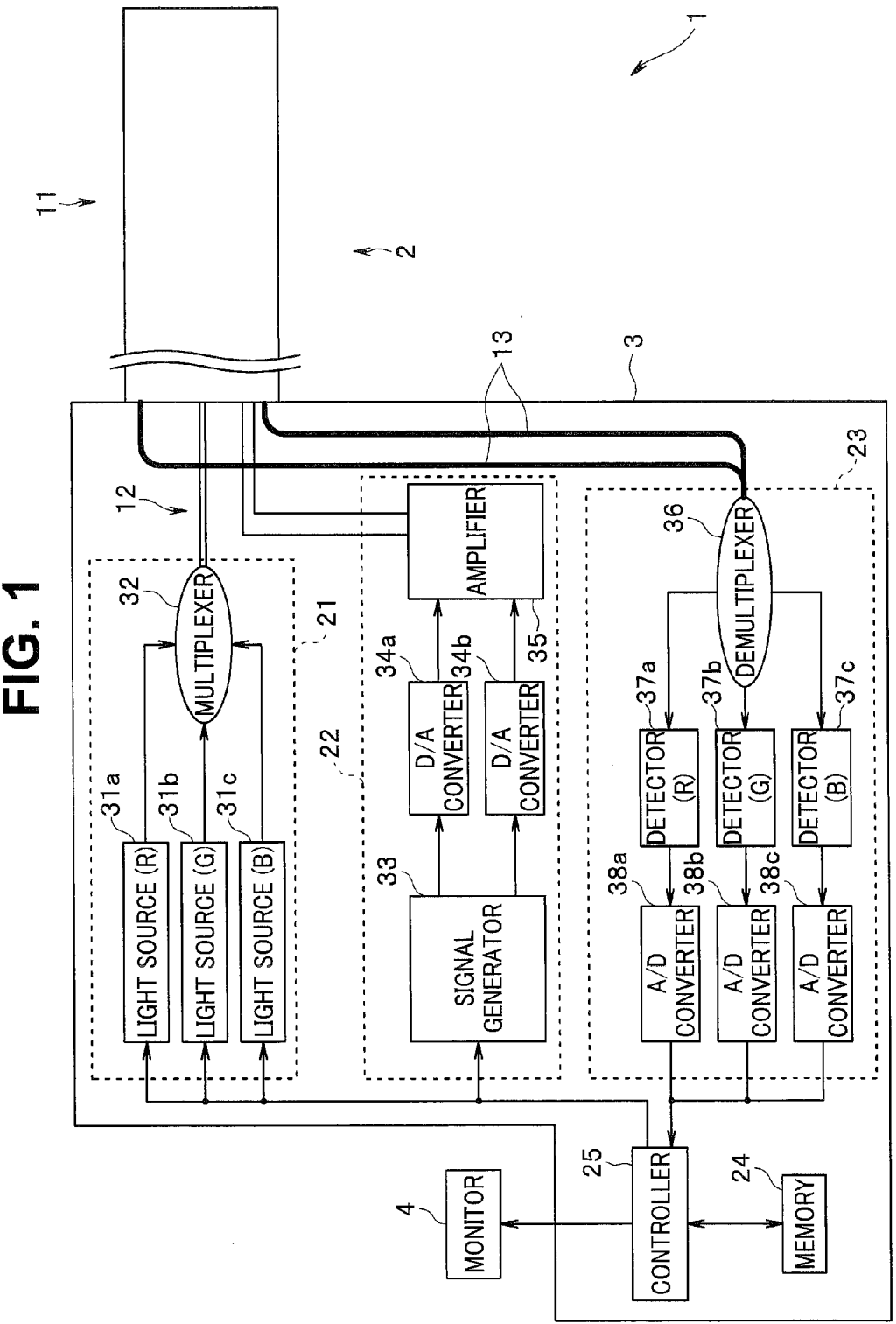
FIG. 1 illustrates a configuration of a main part of a scanning endoscope system including a scanning endoscope according to an embodiment of the present invention.

FIGS. 1 to 4 relate to the first embodiment of the present invention. FIG. 1 illustrates a configuration of a main part of a scanning endoscope system including a scanning endoscope according to an embodiment of the present invention.

A scanning endoscope system 1 includes, as shown in FIG. 1 for example, a scanning endoscope 2 configured to be insertable into a body cavity of a subject to be examined, a main body apparatus 3 connected to the scanning endoscope 2, and a monitor 4 connected to the main body apparatus 3.

The scanning endoscope 2 includes an insertion portion 11 formed in an elongated cylindrical shape and having flexibility. In addition, the insertion portion 11 includes, at the proximal end portion thereof, a connector, for example, not shown, for detachably connecting the scanning endoscope 2 to the main body apparatus 3.

Figure 2:
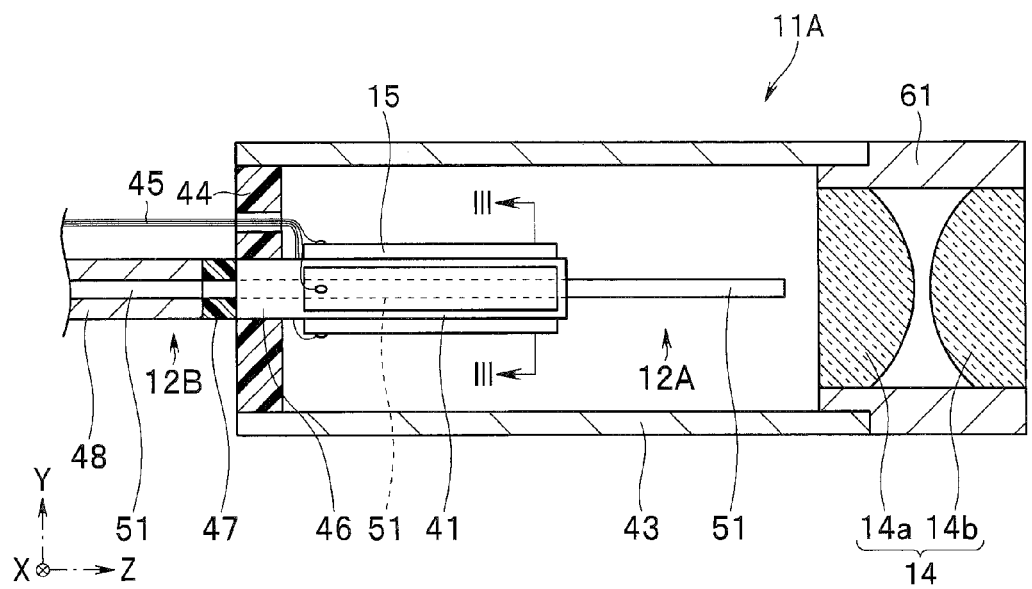
FIG. 2 illustrates one example of a configuration of a distal end portion of a scanning endoscope according to a first embodiment.

FIG. 2 illustrates one example of a configuration of a distal end portion of the scanning endoscope according to the first embodiment. As shown in FIG. 2, the insertion portion 11 includes, at a distal end portion 11A, a light-emission-side end portion of a light-guiding portion for illumination 12 configured to guide illumination light supplied from the main body apparatus 3 with an optical fiber 51 to allow the illumination light to emit from a light emission surface positioned on the distal end side of the optical fiber 51, a light condensing optical system 14 configured to condense the illumination light emitted from the light-guiding portion for illumination 12, the light condensing optical system 14 being arranged so as to be fixed by a lens frame 61, and an actuator portion 15 provided at the light-emission-side end portion of the light-guiding portion for illumination 12 and configured to vibrate in response to a driving signal supplied through a plurality of signal lines 45 connected to the main body apparatus 3, to thereby enable a part of the optical fiber 51 which is located in the light emission portion 12A of the light-guiding portion for illumination 12 to oscillate. Note that, though not shown in FIG. 2, the distal end portion 11A of the insertion portion 11 includes a light-incident-side end portion of a light-guiding portion for light reception 13 that receives return light from the object to guide the received return light to the main body apparatus 3.

The optical fiber 51 is formed by including a core (not shown) which is a propagation path of the illumination light supplied from the main body apparatus 3 and a clad (not shown) covering around the core.

In the light-emission-side end portion of the light-guiding portion for illumination 12, a part of the optical fiber 51 located in the light emission portion 12A including the light emission surface is disposed in the state not covered with a vibration-absorbing member 47 and a fiber outer cover 48. Furthermore, in the light-emission-side end portion of the light-guiding portion for illumination 12, another part of the optical fiber 51 located in the light transmission portion 12B which does not include the light emission surface is disposed in the state covered with the vibration-absorbing member 47 and the fiber outer cover 48.

Each of the lenses 14a and 14b of the light condensing optical system 14 are configured to have a positive refractive power.

As shown in FIG. 2, the part of the optical fiber 51 which is located in the light emission portion 12A is arranged so as to penetrate through the distal end portion 11A of the insertion portion 11, and the distal end portion 11A of the insertion portion 11 is provided with: a ferrule 41 including on the outer surface thereof the actuator portion 15; a housing 43 made of a hollow cylindrical-shaped metal or the like; a holding member 44 which holds the actuator portion 15 and the ferrule 41 in the housing 43; the plurality of signal lines 45; the vibration-absorbing member 47; and the fiber outer cover 48.

Figure 3:
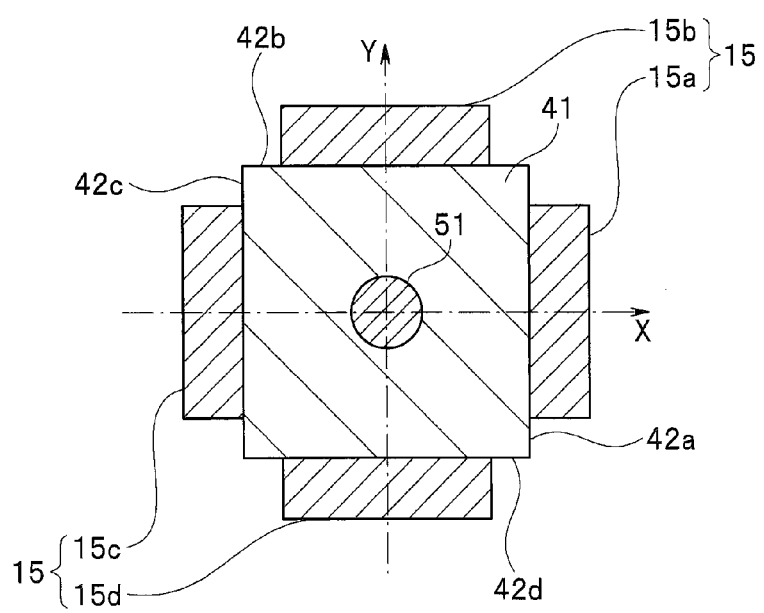
FIG. 3 is a cross-sectional view taken along III-III line in FIG. 2.

FIG. 3 is a cross-sectional view taken along the III-III line in FIG. 2. As shown in FIG. 3, the ferrule 41 as a joint member is arranged between the optical fiber 51 and the actuator portion 15. Specifically, the ferrule 41 is made of zirconia (ceramic) or nickel, etc., for example.

As shown in FIG. 3, the ferrule 41 is formed as a quadrangular prism and includes side surfaces 42a and 42c which are vertical to the X-axis direction and side surfaces 42b and 42d which are vertical to the Y-axis direction. In addition, at the center of the ferrule 41, the part of the optical fiber 51 which is located on the proximal end side of the light emission portion 12A is fixedly arranged. Note that the ferrule 41 may be formed in another shape other than quadrangular prism, as long as the ferrule has a rectangular prism shape.

As shown in FIG. 3, the actuator portion 15 includes an actuator 15a arranged along the side surface 42a, an actuator 15b arranged along the side surface 42b, an actuator 15c arranged along the side surface 42c, and an actuator 15d arranged along the side surface 42d.

The actuators 15a and 15c are, for example, made of piezoelectric elements and configured to vibrate in response to a driving signal outputted from an amplifier 35 through a D/A converter 34a of a driver unit 22.

The actuators 15b and 15d are, for example, made of piezoelectric elements and configured to vibrate in response to a driving signal outputted from the amplifier 35 through the D/A converter 34b of the driver unit 22.

As shown in FIG. 2, the housing 43 is formed so as to have an inner diameter enough to cover around the light-emission-side end portion of the light-guiding portion for illumination 12, the actuator portion 15 and the ferrule 41. In addition, as shown in FIG. 2, the distal end side of the housing 43 is coupled to a predetermined position on the proximal end side of the lens frame 61.

As shown in FIG. 2, the holding member 44 is formed such that a plane (hereinafter, also referred to as the XY plane), which is perpendicular to a longitudinal direction (hereinafter, also referred to as the Z-axis direction) of the light-guiding portion for illumination 12, has substantially a ring shape, for example. In addition, the holding member 44 is mounted in the state where the surface (side surface) parallel to the Z-axis direction is brought into contact with the inner circumferential surface of the housing 43. Further, the holding member 44 includes a hole portion into which a ferrule proximal end portion 46, which is located at a position away from the arranging position of the actuator portion 15 toward the proximal end side, can be fitted. Furthermore, the holding member 44 includes an insertion hole through which the plurality of signal lines 45 can be inserted. That is, with the configuration of the holding member 44 as described above, the ferrule proximal end portion 46 of the ferrule 41 is fitted in the hole portion of the holding member 44, and thereby the part of the optical fiber 51 which is located in the light emission portion 12A, the actuator portion 15 connected to the plurality of signal lines 45, and the ferrule 41 are held in a cantilevered manner in the internal space of the housing 43.

The vibration-absorbing member 47 is, for example, made of an adhesive or a soft rubber and the like, and formed so as to cover a circumference of a portion of the optical fiber adjacent to the holding member 44 (or the ferrule proximal end portion 46 fitted into the hole portion of the holding member 44), the portion being included in the part of the optical fiber 51 which is located in the light transmission portion 12B.

The fiber outer cover 48 is formed so as to cover a circumference of at least one portion located on the proximal end side with respect to the portion covered with the vibration-absorbing member 47, the one portion being included in the part of the optical fiber 51 which is located in the light transmission portion 12B.

That is, with the configuration as described above, the part of the optical fiber 51 from the light emission surface to the inside of the ferrule 41 is located in the light emission portion 12A, and the other part of the optical fiber 51, which extends outward (toward the proximal end side) from the ferrule proximal end portion 46, is located in the light transmission portion 12B. Note that, in the present embodiment, such a division between the light emission portion 12A and the light transmission portion 12B is applied not only to the distal end portion 11A but also to a distal end portion 11B to be described later.

The main body apparatus 3 includes a light source unit 21, the driver unit 22, a detection unit 23, a memory 24, and a controller 25.

The light source unit 21 includes a function as a light source portion that supplies illumination light for illuminating an object. Specifically, as shown in FIG. 1, the light source unit 21 includes a light source 31a, a light source 31b, a light source 31c, and a multiplexer 32.

The light source 31a includes a laser light source, etc., for example, and configured to emit light in the red wavelength band (hereinafter, also referred to as R light) to the multiplexer 32, when turned on under the control by the controller 25.

The light source 31b includes a laser light source, etc., for example, and configured to emit light in the green wavelength band (hereinafter, also referred to as G light) to the multiplexer 32, when turned on under the control by the controller 25.

The light source 31c includes a laser light source, etc., for example, and configured to emit light in the blue wavelength band (hereinafter, also referred to as B light) to the multiplexer 32, when turned on under the control by the controller 25.

The multiplexer 32 is configured to multiplex the R light emitted from the light source 31a, the G light emitted from the light source 31b, and the B light emitted from the light source 31c and supply the multiplexed light onto the light incident surface of the light-guiding portion for illumination 12.

As shown in FIG. 1, the driver unit 22 includes a signal generator 33, D/A converters 34a, 34b, and the amplifier 35.

The signal generator 33 is configured to generate a driving signal for causing the light-guiding portion for illumination 12 to oscillate, and configured to output the driving signal to the D/A converters 34a, 34b under the control by the controller 25.

Each of the D/A converters 34a and 34b is configured to convert a digital driving signal outputted from the signal generator 33 into an analog driving signal to output the analog driving signal to the amplifier 35.

The amplifier 35 is configured to amplify the driving signal outputted from each of the D/A converters 34a and 34b, to output the amplified driving signal to the actuator portion 15.

As shown in FIG. 1, the detection unit 23 includes a demultiplexer 36, detectors 37a, 37b, and 37c, and A/D converters 38a, 38b, and 38c.

The demultiplexer 36 includes a dichroic mirror and the like and configured to separate the return light emitted from the light emission surface of the light-guiding portion for light reception 13 into light of each color component of R (red), G (green), and B (blue), and emit the separated light to each of the detectors 37a, 37b and 37c.

The detector 37a is configured to detect the intensity of the R light outputted from the demultiplexer 36, generate an analog R signal corresponding to the detected intensity of the R light, and output the generated analog R signal to the A/D converter 38a.

The detector 37b is configured to detect the intensity of the G light outputted from the demultiplexer 36, generate an analog G signal corresponding to the detected intensity of the G light, and output the generated analog G signal to the A/D converter 38b.

The detector 37c is configured to detect the intensity of the B light outputted from the demultiplexer 36, generate an analog B signal corresponding to the detected intensity of the B light, and output the generated analog B signal to the A/D converter 38c.

The A/D converter 38a is configured to convert the analog R signal outputted from the detector 37a into a digital R signal, to output the digital R signal to the controller 25.

The A/D converter 38b is configured to convert the analog G signal outputted from the detector 37b into a digital G signal, to output the digital G signal to the controller 25.

The A/D converter 38c is configured to convert the analog B signal outputted from the detector 37c into a digital B signal, to output the digital B signal to the controller 25.

A memory 24 previously stores a control program for controlling the main body apparatus 3, etc.

The controller 25 includes a CPU, etc., and is configured to read the control program stored in the memory 24 and control the light source unit 21 and the driver unit 22 based on the read control program. That is, the actuator portion 15 vibrates based on the driving signal supplied from the driver unit 22 according to the above-described control by the controller 25, thereby capable of oscillating the part of the optical fiber 51 which is located in the light emission portion 12A of the light-guiding portion for illumination 12 such that the irradiation position of the illumination light with which the object is irradiated draws a trajectory corresponding to a predetermined scanning pattern (for example, spiral shape, Lissajous shape, or the like).

The controller 25 is configured to generate an image based on the R signal, G signal, and B signal outputted from the detection unit 23, to cause the generated image to be displayed on the monitor 4.

Next, description will be made on the working of the scanning endoscope system 1 including the scanning endoscope 2 according to the present embodiment.

Power source of each section of the scanning endoscope system 1 is turned on, and then the controller 25 controls the light source unit 21 to switch the light sources 31a, 31b, and 31c from off to on, based on the control program stored in the memory 24, and controls the driver unit 22 to cause the signal generator 33 to output a driving signal for oscillating the light-guiding portion for illumination 12 in a predetermined scanning pattern. According to such control by the controller 25, the driver unit 22 supplies a driving signal to the actuator portion 15, and in response to the supplied driving signal, the actuator portion 15 vibrates, to cause the part of the optical fiber 51 which is located in the light emission portion 12A to oscillate in the predetermined scanning pattern, and then mixed light of R light, G light and B light is emitted from the light emission surface of the optical fiber 51 as illumination light.

According to the above-described configuration of the distal end portion 11A, in the part of the optical fiber 51 which is located in the light transmission portion 12B, the portion adjacent to the holding member 44 (or the ferrule proximal end portion 46 fitted into the hole portion of the holding member 44) is covered with the vibration-absorbing member 47. Therefore, according to the above-described configuration of the distal end portion 11A, the vibration of the actuator portion 15 to be transmitted toward the ferrule proximal end portion 46, is absorbed by the vibration-absorbing member 47, which prevents the part (not directly related to the scanning of the object) of the optical fiber 51 which is located in the light transmission portion 12B from oscillating in accordance with the vibration of the actuator portion 15. As a result, with the scanning endoscope 2 including the distal end portion 11A, only the part (directly related to the scanning of the object) of the optical fiber 51 which is located in the light emission portion 12A can be oscillated in accordance with the vibration of the actuator portion 15, which enables a stable scanning of the object to be performed.

Figure 4:
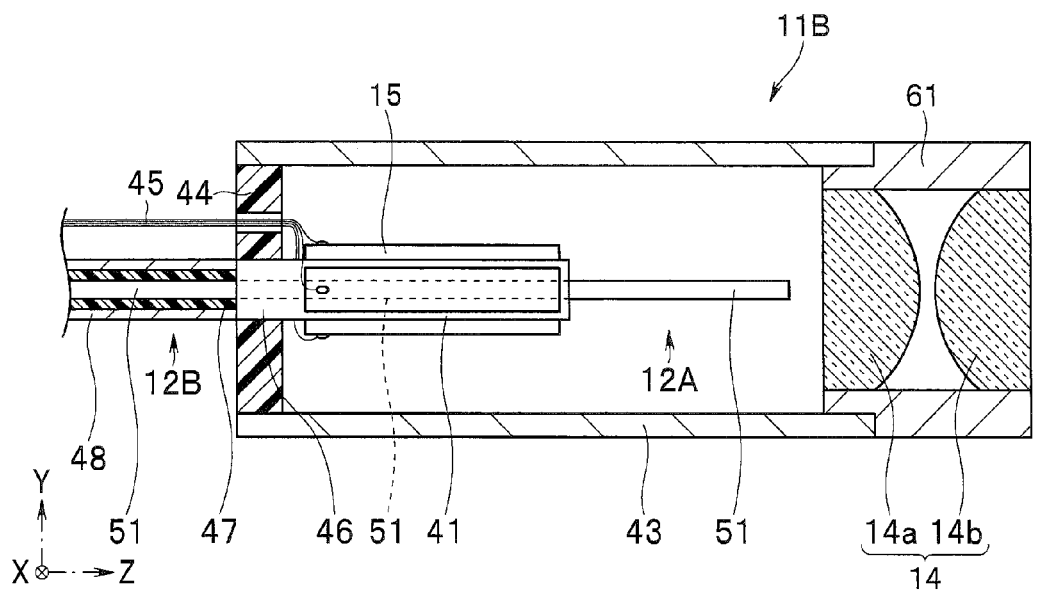
FIG. 4 illustrates an example of the configuration of the distal end portion of the scanning endoscope according to the first embodiment, the example being different from the one in FIG. 2.

Alternatively, in the present embodiment, the scanning endoscope 2 may be provided with a distal end portion 11B as shown in FIG. 4, for example, instead of the distal end portion 11A as shown in FIG. 2. FIG. 4 illustrates an example of the configuration of the distal end portion of the scanning endoscope according to the first embodiment, the example being different from the one in FIG. 2. Note that, hereinafter, detailed description on the components having the same configurations as those of the distal end portion 11A is omitted for simplification, and components having configurations different from those of the distal end portion 11A are mainly described.

As shown in FIG. 4, the distal end portion 11B is configured such that the part of the optical fiber 51, which is located in the light transmission portion 12B, is covered in a covering method different from the one used for the distal end portion 11A.

Specifically, the distal end portion 11B includes a vibration-absorbing member 47 configured to cover the circumference of the part of the optical fiber 51 which is located in the light transmission portion 12B, and a fiber outer cover 48 configured to cover the circumference of at least a part of the vibration-absorbing member 47. In other words, in the distal end portion 11B, the part of the optical fiber 51 which is located in the light transmission portion 12B is doubly covered with the vibration-absorbing member 47 and the fiber outer cover 48. In addition, according to the above-described configuration of the distal end portion 11B, in the part of the optical fiber 51 which is located in the light transmission portion 12B, the circumference of the portion adjacent to the holding member 44 (or the ferrule proximal end portion 46 fitted into the hole portion of the holding member 44) is covered with the vibration-absorbing member 47.

Therefore, the scanning endoscope 2 including the distal end portion 11B is capable of preventing the part (not directly related to the scanning of the object) of the optical fiber 51, which is located in the light transmission portion 12B, from oscillating in accordance with the vibration of the actuator portion 15, since the vibration of the actuator portion 15 to be transmitted toward the ferrule proximal end portion 46 is absorbed by the vibration-absorbing member 47. As a result, with the scanning endoscope 2 including the distal end portion 11B, only the part (directly related to the scanning of the object) of the optical fiber 51, which is located in the light emission portion 12A, can be oscillated in accordance with the vibration of the actuator portion 15, which enables a stable scanning of the object to be performed.

Note that, according to the present embodiment, the distal end portion 11A and the distal end portion 11B may be configured to include a composite cable which integrates a plurality of signal lines 45 inserted through the insertion hole of the holding member 44 and the part of the optical fiber 51 (which is located in the light transmission portion 12B) covered with the vibration-absorbing member 47 and the fiber outer cover 48, for example.

Second Embodiment

Figure 5:
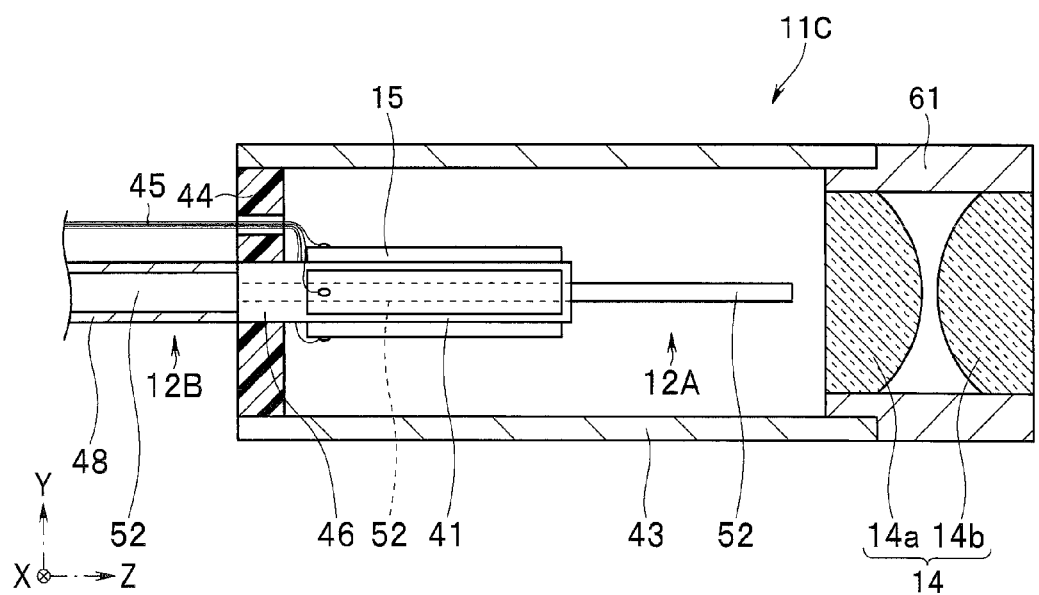
FIG. 5 illustrates one example of a configuration of a distal end portion of a scanning endoscope according to a second embodiment.
Figure 6:
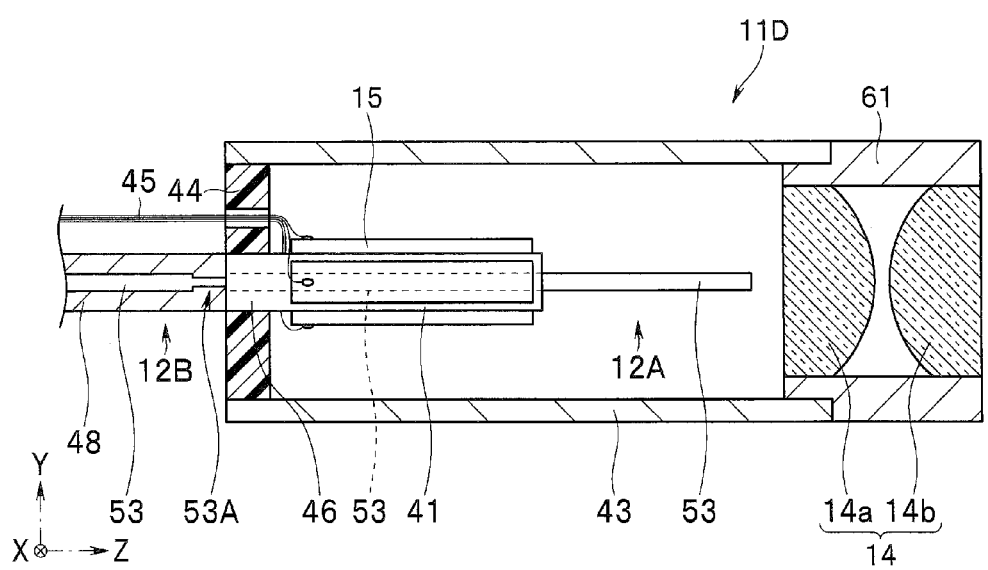
FIG. 6 illustrates an example of the configuration of the distal end portion of the scanning endoscope according to the second embodiment, the example being different from the one in FIG. 5.

FIGS. 5 and 6 relate to the second embodiment of the present invention. FIG. 5 illustrates one example of a configuration of a distal end portion of a scanning endoscope according to the second embodiment.

Note that, in the present embodiment, detailed description on the components having the same configuration as those in the first embodiment is omitted, and components having configurations different from those in the first embodiment are mainly described.

An insertion portion 11 of a scanning endoscope 2 according to the present embodiment includes a distal end portion 11C as shown in FIG. 5, instead of the distal end portion 11A (or distal end portion 11B).

As shown in FIG. 5, the distal end portion 11C has a configuration substantially the same as the configuration in which the vibration-absorbing member 47 is eliminated from the distal end portion 11A (or distal end portion 11B) and an optical fiber 52 is provided instead of the optical fiber 51 of the distal end portion 11A.

The optical fiber 52 includes a core (not shown) as a propagation path of the illumination light supplied from the main body apparatus 3 and a clad (not shown) covering around the core. In addition, the optical fiber 52 is formed such that an outer diameter (clad diameter) of a part located in a light transmission portion 12B is larger than an outer diameter (clad diameter) of a part located in a light emission portion 12A. In other words, the optical fiber 52 is formed such that the outer diameter (clad diameter) of the portion adjacent to the holding member 44, the portion being included in the part located in the light transmission portion 12B, is larger than the outer diameter (clad diameter) of the part located in the light emission portion 12A.

In the light-emission-side end portion of the light-guiding portion for illumination 12, the part of the optical fiber 52 located in the light emission portion 12A is disposed in the state not covered with a fiber outer cover 48. Furthermore, in the light-emission-side end portion of the light-guiding portion for illumination 12, the other part of the optical fiber 52 located in the light transmission portion 12B is disposed in the state covered with the fiber outer cover 48.

That is, according to the configuration as described above, the part of the optical fiber 52, which has a relatively smaller outer diameter (clad diameter), is located in the light emission portion 12A, and the other part of the optical fiber 52, which has a relatively larger outer diameter (clad diameter), is located in the light transmission portion 12B. In addition, according to the configuration of the holding member 44 of the distal end portion 11C, the ferrule proximal end portion 46 of the ferrule 41 is fitted in the hole portion of the holding member 44, and thereby the part of the optical fiber 52 which is located in the light emission portion 12A, the actuator portion 15 connected to the plurality of signal lines 45, and the ferrule 41 are held in a cantilevered manner in the internal space of the housing 43.

Next, description will be made on the working of the scanning endoscope system 1 including the scanning endoscope 2 according to the present embodiment.

Power source of each section of the scanning endoscope system 1 is turned on, and then the controller 25 controls the light source unit 21 to switch the light sources 31a, 31b, and 31c from off to on, based on the control program stored in the memory 24, and controls the driver unit 22 to cause the signal generator 33 to output a driving signal for oscillating the light-guiding portion for illumination 12 in a predetermined scanning pattern. According to such control by the controller 25, the driver unit 22 supplies a driving signal to the actuator portion 15, and in response to the supplied driving signal, the actuator portion 15 vibrates, to cause the part of the optical fiber 52 which is located in the light emission portion 12A to oscillate in the predetermined scanning pattern, and then mixed light of R light, G light and B light is emitted from the light emission surface of the optical fiber 52 as illumination light.

According to the above-described configuration of the distal end portion 11C, the outer diameter (clad diameter) of the part of the optical fiber 52 located in the light emission portion 12A is different from that of the other part of the optical fiber 52 located in the light transmission portion 12B. Therefore, according to the above-described configuration of the distal end portion 11C, the vibration of the actuator portion 15 to be transmitted toward the ferrule proximal end portion 46 is reflected on (XY plane corresponding to) the border surface of the parts of the optical fiber 52 between the light emission portion 12A and the light transmission portion 12B, thereby preventing the other part (not directly related to the scanning of the object) of the optical fiber 52, which is located in the light transmission portion 12B, from oscillating in accordance with the vibration of the actuator portion 15. As a result, the scanning endoscope 2 including the distal end portion 11C is capable of causing only the part (directly related to the scanning of the object) of the optical fiber 52, which is located in the light emission portion 12A, to oscillate in accordance with the vibration of the actuator portion 15, thereby enabling stable scanning of the object to be performed.

In the present embodiment, the scanning endoscope 2 may be provided with a distal end portion 11D as shown in FIG. 6, for example, instead of the distal end portion 11C as shown in FIG. 5. FIG. 6 illustrates an example of the configuration of the distal end portion of the scanning endoscope according to the second embodiment, the example being different from the one in FIG. 5. Note that, hereinafter, detailed description on the components having the same configurations as those of the distal end portion 11C is omitted for simplification, and components having configurations different from those of the distal end portion 11C are mainly described.

As shown in FIG. 6, the distal end portion 11D has a configuration substantially the same as the configuration in which the vibration-absorbing member 47 is eliminated from the distal end portion 11A (or distal end portion 11B) and an optical fiber 53 is provided instead of the optical fiber 51 of the distal end portion 11A.

The optical fiber 53 includes a core (not shown) as a propagation path of the illumination light supplied from the main body apparatus 3 and a clad (not shown) covering around the core. In addition, the optical fiber 53 includes a reduced-diameter portion 53A in a predetermined range adjacent to the holding member 44 (or the ferrule proximal end portion 46 fitted into the hole portion of the holding member 44), the range being included in a part of the optical fiber 53 which is located in the light transmission portion 12B.

The reduced-diameter portion 53A is formed so as to have an outer diameter (clad diameter) smaller than the outer diameter (clad diameter) of the part of the optical fiber 53 which is located in the light emission portion 12A. Note that, in the present embodiment, the outer diameter (clad diameter) of a portion other than the reduced-diameter portion 53A of the part of the optical fiber 53 which is located in the light transmission portion 12B is substantially equal to the outer diameter (clad diameter) of the part of the optical fiber 53 which is located in the light emission portion 12A.

In the light-emission-side end portion of the light-guiding portion for illumination 12, the part of the optical fiber 53 located in the light emission portion 12A is disposed in the state not covered with a fiber outer cover 48. Furthermore, in the light-emission-side end portion of the light-guiding portion for illumination 12, the part of the optical fiber 53 located in the light transmission portion 12B, which includes the diameter-reduced portion 53A, is disposed in the state covered with the fiber outer cover 48.

That is, with the configuration as described above, the part of the optical fiber 53, which is formed so as to have a uniform outer diameter (clad diameter), is located in the light emission portion 12A, and the part of the optical fiber 53, which has a non-uniform outer diameter (clad diameter) at the diameter-reduced portion 53A, is located in the light transmission portion 12B. In addition, according to the configuration of the holding member 44 of the distal end portion 11D, the ferrule proximal end portion 46 of the ferrule 41 is fitted in the hole portion of the holding member 44, and thereby the part of the optical fiber 53 which is located in the light emission portion 12A, the actuator portion 15 connected to the plurality of signal lines 45, and the ferrule 41 are held in a cantilevered manner in the internal space of the housing 43.

Therefore, according to the scanning endoscope 2 including the distal end portion 11D, the vibration of the actuator portion 15 to be transmitted toward the ferrule proximal end portion 46 is reflected on (XY plane corresponding to) the border surface of the parts of the optical fiber 53 between the light emission portion 12A and the light transmission portion 12B, thereby preventing the part (not directly related to the scanning of the object) of the optical fiber 53, which is located in the light transmission portion 12B, from oscillating in accordance with the vibration of the actuator portion 15. As a result, with the scanning endoscope 2 including the distal end portion 11D, only the part (directly related to the scanning of the object) of the optical fiber 53, which is located in the light emission portion 12A, can be oscillated in accordance with the vibration of the actuator portion 15, which enables a stable scanning of the object to be performed.

It is needless to say that the present invention is not limited to the above-described embodiments, and various changes and modifications are possible in a range without departing from the gist of the invention.

What is claimed is:

1. A scanning endoscope comprising:
    an optical fiber that guides illumination light for illuminating an object from a proximal end thereof and emits the illumination light from a distal end thereof;
    a joint member formed entirely in a quadrangular prism shape, the joint member having an insertion hole in which the optical fiber is inserted, an inner surface of the insertion hole directly contacting the optical fiber;
    an actuator portion that causes the distal end of the optical fiber to oscillate, the actuator portion being provided on an outer surface of the joint member;
    a holding portion that holds the joint member so as to allow the distal end of the optical fiber to oscillate with the actuator portion, the holding portion having an inner surface directly contacting the joint member, and the holding portion being provided on a more proximal end side of the optical fiber than the actuator portion;
    a vibration-absorbing member formed so as to directly cover a circumference of a part of the optical fiber and to directly contact the joint member, the part being located on a more proximal end side than the holding portion, the vibration-absorbing member being made of a material that absorbs vibration; and
    an outer cover that directly covers and contacts a circumference of at least a part of the vibration-absorbing member.

2. The scanning endoscope according to claim 1, wherein the outer cover further covers a circumference of at least a part of the optical fiber, the part being located on the proximal end side with respect to the portion covered with the vibration-absorbing member.

3. The scanning endoscope according to claim 1,
wherein the joint member is formed as a rectangular prism having a hole in which the optical fiber is inserted, and
the actuator portion has a plurality of actuators each of which is arranged along a side surface of the rectangular prism.

* * * * *